United States Patent
Olson et al.

(10) Patent No.: US 10,267,783 B2
(45) Date of Patent: Apr. 23, 2019

(54) SUBMERSIBLE FLOW IMAGER

(71) Applicant: Woods Hole Oceanographic Institution, Woods Hole, MA (US)

(72) Inventors: Robert J. Olson, Cataumet, MA (US); Heidi M. Sosik, Falmouth, MA (US)

(73) Assignee: Woods Hole Oceanographic Institution, Woods Hole, MA (US)

( * ) Notice: Subject to any disclaimer, the term of this patent is extended or adjusted under 35 U.S.C. 154(b) by 0 days.

(21) Appl. No.: 14/480,871

(22) Filed: Sep. 9, 2014

(65) Prior Publication Data
US 2015/0125944 A1 May 7, 2015

Related U.S. Application Data

(60) Provisional application No. 61/875,253, filed on Sep. 9, 2013.

(51) Int. Cl.
*G01N 33/18* (2006.01)
*G01N 15/14* (2006.01)
*G01N 15/00* (2006.01)

(52) U.S. Cl.
CPC ..... *G01N 33/1886* (2013.01); *G01N 15/1404* (2013.01); *G01N 15/1459* (2013.01); *G01N 2015/0053* (2013.01); *G01N 2015/149* (2013.01); *G01N 2015/1413* (2013.01)

(58) Field of Classification Search
CPC .. G01N 15/147; G01N 21/05; G01N 21/6456; G01N 21/6486
See application file for complete search history.

(56) References Cited

U.S. PATENT DOCUMENTS

| | | | | |
|---|---|---|---|---|
| 4,571,984 | A * | 2/1986 | Malcosky | G01N 29/032 73/19.03 |
| 5,030,002 | A * | 7/1991 | North, Jr. | G01N 15/1404 209/3.1 |
| 5,408,326 | A * | 4/1995 | Wang | G01N 21/255 250/576 |
| 6,119,630 | A * | 9/2000 | Lobsiger et al. | 119/238 |
| 6,536,272 | B1 * | 3/2003 | Houston | G01N 1/12 702/2 |
| 6,746,873 | B1 * | 6/2004 | Buchanan | G01N 15/1404 209/127.4 |

(Continued)

FOREIGN PATENT DOCUMENTS

WO    WO 2012144955 A1 * 10/2012 ............. G01N 21/05

*Primary Examiner* — Matthew D Krcha
(74) *Attorney, Agent, or Firm* — Robert Devin Ricci; Jessica C. Engler; Kean Miller LLP

(57) ABSTRACT

Submersible technology capable of sampling and evaluating suspended particulate materials, including living and dead organisms, is disclosed herein. In addition to fluorescent imaging and analysis, the invention provides automated cell staining, cell sorting, particulate concentration, and organism recovery and preservation. These new technologies may be incorporated into a traditional "fully vertical flow path" cytometer configuration most suitable for anchored or suspended stationary embodiments, or in a novel modularized "low relief" configuration, suitable for integration into or on a submersible aquatic vehicle or in other low clearance installations, where it is important to limit the vertical height of the device.

23 Claims, 9 Drawing Sheets

(56) References Cited

U.S. PATENT DOCUMENTS

| | | | |
|---|---|---|---|
| 7,070,739 B1* | 7/2006 | Anderson et al. | 422/82.05 |
| 2002/0171827 A1* | 11/2002 | van den Engh | G01N 15/1434 356/317 |
| 2004/0025602 A1* | 2/2004 | Norton | G01N 15/1459 73/863.21 |
| 2006/0021437 A1* | 2/2006 | Kaduchak | G01N 15/1459 73/570.5 |
| 2009/0109432 A1* | 4/2009 | Olson et al. | 356/244 |
| 2010/0266156 A1* | 10/2010 | Bishop | 382/100 |
| 2011/0141466 A1* | 6/2011 | Magnusson | B01L 3/502715 356/319 |

\* cited by examiner

US 10,267,783 B2

SUBMERSIBLE FLOW IMAGER

CROSS REFERENCE TO RELATED APPLICATIONS

This application claims priority to the provisional U.S. patent application 61/875,253 entitled "Submersible Flow Imager" filed Sep. 9, 2013.

STATEMENT REGARDING FEDERALLY SPONSORED RESEARCH OR DEVELOPMENT

This invention was made with government support under Grants OCE-1130140 and OCE-1428703 awarded by the National Science Foundation. The government has certain rights in the invention.

REFERENCE TO A "SEQUENCE LISTING," A TABLE, OR A COMPUTER PROGRAM

Not Applicable.

DESCRIPTION OF THE DRAWINGS

The drawings constitute a part of this specification and include exemplary embodiments of the submersible flow imager, which may be embodied in various forms. It is to be understood that in some instances, various aspects of the invention may be shown exaggerated or enlarged to facilitate an understanding of the invention. Therefore the drawings may not be to scale.

FIG. 1 depicts the submersible flow imager in a substantially vertical orientation. For operation in a substantially horizontal orientation, the location of the components would be the same except rotated approximately 90 degrees clockwise (or counter-clockwise).

DETAILED DESCRIPTION

Figure 1:
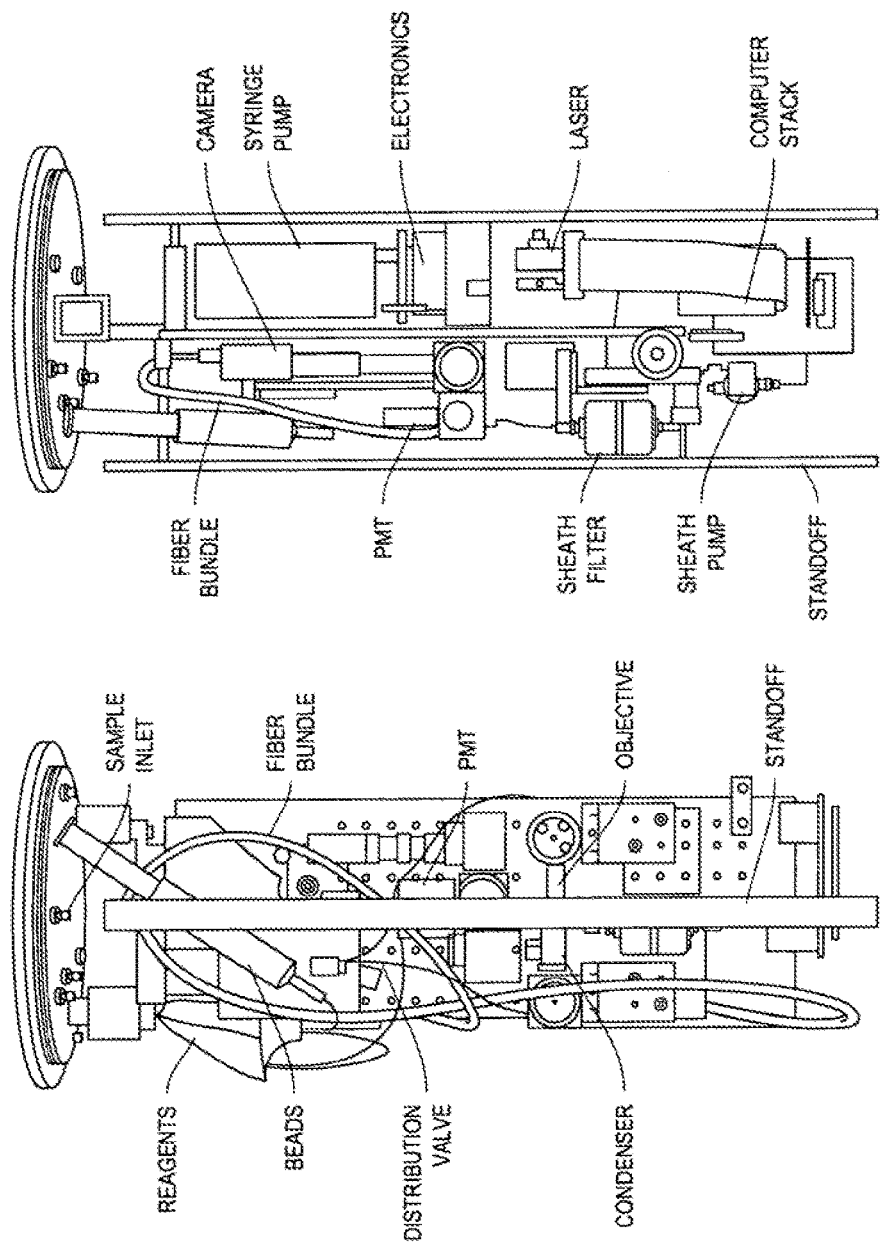
FIG. 1 shows an embodiment of the submersible flow imager when it is removed from its housing. Three plastic standoffs prevent contact of the components and housing during installation. The left image is a front view, showing the "fluidics and optics" side of the optical systems. The flow cell (hidden by standoff) is located between the condenser and objective lenses. The right image is a side view and the optical system is edge-on in the center with the fluidics/optics components mounted to the left and the electronics to the right.

The systems, apparatus, and methods described herein relate to a submersible flow imaging apparatus that can sample, monitor, evaluate, and/or preserve individual microorganisms in aquatic environments by imbibing liquid samples and processing them according to the features described herein.

The system, apparatus, and methods of the submersible flow imager are described with specificity herein to meet statutory requirements. However, the description itself is not intended to necessarily limit the scope of claims. Rather, the claimed subject matter might be embodied in other ways to include different steps or combinations of steps similar to the ones described in this document, in conjunction with other present or future technologies. Although the terms "step" and/or "block" or "module" etc. might be used herein to connote different components of methods or systems employed, the terms should not be interpreted as implying any particular order among or between various steps herein disclosed unless and except when the order of individual steps is explicitly described.

Furthermore, the described features, structures, or characteristics may be combined in any suitable manner in one or more embodiments. One skilled in the relevant art will recognize, that the submersible flow imager and its systems and methods may be practiced without one or more of the specific details, or with other methods, components, materials, and so forth. In other instances, well-known structures, materials, or operations are not shown or described in detail to avoid obscuring aspects of the invention.

The entire specification, drawings, and claims of, now abandoned, U.S. patent application Ser. No. 11/978,246 (Publication No. U.S. 2009/0109432 A1), filed on Oct. 26, 2007, titled "Systems and Methods for Submersible Imaging Flow Apparatus" are completely incorporated in this application by reference.

In the face of aquatic pollution, climate change, and other environmental challenges which impact aquatic life, the ability to evaluate the status of the microscopic aquatic biome has significant commercial importance. Plankton in the size range of 10-100 micron, including many diatoms and dinoflagellates, are one critical component of aquatic ecosystems, but due to the difficulties with sampling in dynamic aquatic environments many aspects of their status and distribution are poorly understood.

In the past, submersible flow cytometers were used to measure fluorescence and light scattering signals from a laser beam to characterize the smallest phytoplankton cells (approximately 1-10 µm). Other commercially available instruments, such as the Video Plankton Recorder are capable of monitoring plankton at the other end of the size spectrum (mainly zooplankton >approximately 100 µm). However, plankton in the size range of approximately 10-100 µm are not well sampled by either of these instruments. This is a critical gap because phytoplankton in this size range, which includes many diatoms and dinoflagellates, can be especially important in coastal blooms, while microzooplankton, such as protozoa, are critical to the diets of many grazers including copepods and larval fish.

Other submersible flow cytometers have been developed, such as the FlowCAM and the CytoSub, but none has the necessary resolution and field endurance for many of the needed ecological studies. The FlowCAM differs from the submersible flow imager disclosed herein (marketed under the name "Imaging FlowCytobot" and also referred to herein as "IFCB") in that the FlowCAM does not utilize hydrodynamic focusing of the sample flow inside a particle-free sheath fluid; FlowCAM is therefore subject to flow cell fouling by particles adhering to the flow cell walls. Lack of the hydrodynamic focusing of sample also means that many images taken by FlowCAM are out of optical focus. The submersible flow imager described herein differs from the CytoSub in that the IFCB disclosed herein is primarily an imaging instrument and captures a high-quality image of every triggering particle, while the CytoSub uses imaging only for identification of user-specified regions of light scattering and fluorescence signatures. In addition, images from the CytoSub are of lower quality than those from the IFCB, as indicated by the Alexandrium (*A. Sanguina*) image on the CytoSub website (http://www.cytobuoy.com/products/benchtop/) accompanied by the statements that its "tail [i.e., flagellum] cannot be seen on the picture, but is present in the pulse shape!" Dinoflagellate flagella are routinely observed in the IFCB images. Neither the FlowCAM nor CytoSub has demonstrated the capability for continuous operation in the field over 6 months' duration deployments, as has the IFCB.

As used herein, references to the words "vertical" or "vertically oriented" mean that the element discussed is substantially aligned with the direction of gravity. For example, if the term "vertically oriented" is used to describe the flow path, or other pathway, it means that the flow path or other pathway is substantially positioned such that the particles flow through the pathway in the direction of the gravitational pull of the earth on such particles. The term "non-vertical orientation," as used herein, includes any orientation that is not "substantially vertical," including, but not limited to, orientations that are substantially horizontal.

As used herein, the terms "particles" or "particulate matter" includes within its definition cells and organisms, even if a specific reference to cells and/or organisms is not made.

According to various aspects, the disclosure herein relates to an apparatus, systems, and associated methods for imaging particles within liquid suspensions. The submersible flow imager comprises a flow system, a detection system, and an electronics system. The flow system is the means by which the sample particles are imbibed into the submersible flow imager, transported through the different modules or other systems of the submersible flow imager, and then either stored or discarded from the submersible flow imager. The electronics system provides control both for the flow system, in controlling the movement of the suspensions within the flow path, and the detection system, in controlling the detection of the particles within the suspension. The electronics system also provides for data storage and data transmission.

The submersible flow imager comprises a flow system, a detection system, an electronics system, and a housing. Each of these systems is described below. Specific embodiments of the submersible flow imager may employ multiple versions of any particular system (flow system, detection system, and/or electronics system) described herein depending on the particular application of the submersible flow imager. The housing may comprise any material known in the art to be suitable for the conditions in which the submersible flow imager will be deployed; such materials include metals, plastics, polymers, ceramics, etc. In a one embodiment the housing is fabricated from aluminum. In one embodiment, the submersible flow imager further comprises a mounting interface for mounting the submersible flow imager onto a vessel, vehicle, or platform. The mounting interface is the means by which the attaching means is attached to the housing. The mounting interface comprises any interface known in the art for use in attaching items to each other, including attached metal loops and having the housing formed such that a cutout in the housing can have a cable/rope passed through it to secure the housing to another object. In another embodiment, the submersible flow imager housing comprises an attachment means for attaching the submersible flow imager to a vessel, vehicle, or platform for towing. In one embodiment, the attachment means provides a means of removably attaching the submersible flow imager to a vessel, vehicle, or platform. In another embodiment, the attachment means provides a means for permanently attaching the submersible flow imager to a vessel, vehicle, or platform. The attachment means can be any attachment means known in the art, such as hook and latch, metal or plastic fasteners, ropes, cable, welding, etc. In one embodiment, the submersible flow imager is operational (imbibing sample particles) while being towed. In another embodiment, the submersible imager is operational (imbibing sample particles) while being in a substantially stationary position. In another embodiment, the submersible flow imager is operational (imbibing sample particles) while being located in strong wave action areas.

Operation of the submersible flow imager in the water in a towed arrangement (either while being towed or while stationary), simplifies temperature control and elimination of particles and sheath fluid. Additionally, operation of the submersible flow imager under water, results in the submersible flow imager being exposed to less motion, from wave action or other causes, thus enhancing the operation of the submersible flow imager. Further, operation of the submersible flow imager under water allows samples to be taken at different depths. In one embodiment, the depth at which samples are imbibed is controlled through the adjustment of the towing angle. In a further embodiment, the submersible flow imager comprises a pressure (depth) sensor to detect the depth at which samples are imbibed. In another embodiment, the depth at which samples are imbibed comprises adjusting the speed of the vehicle, vessel, or platform while the sample is being imbibed.

In another embodiment, the submersible flow imager is deployed in the hull of a vessel, vehicle, or platform. In one embodiment, the flow cell remains substantially vertical while the other aspects of the submersible flow imager are substantially horizontal. In another embodiment, the flow cell remains substantially vertical while the other aspects of the submersible flow imager are positioned in a non-vertical orientation. In another embodiment, all aspects of the submersible flow imager are positioned in a non-vertical orientation. In yet another embodiment, all aspects of the submersible flow imager are substantially horizontal.

In one embodiment, the submersible flow imager is modularized. In this embodiment, at least one module is located in a separate housing than the other modules. In this embodiment, the modules comprise the flow system, the optical system, and the electronics system. In one embodiment, the flow system module and the optical system module are in one housing while the electronic system module is in a separate housing. In another embodiment, all three modules are each contained it their own separate housings. In yet another embodiment, the electronics system module is comprised by the electronics system of a vessel, vehicle, or platform and the flow system module and the optical system module are located within the same housing. In a further embodiment, the housing where the flow system and optical system modules are located is comprised by the payload bay area of the vessel, vehicle, or platform. In yet another embodiment, the electronics system module is comprised by the electronics system of a vessel, vehicle, or platform and the flow system module and optical system module are located in separate housings from one another. In another embodiment, the optical system module housing is comprised by the payload bay area of a vessel, vehicle, or platform.

Particles to be Analyzed. The submersible flow imager is used to obtain and evaluate liquid samples containing suspended particulate matter including inanimate as well as living and/or dead cells/organisms. In some embodiments, the particles are autofluorescent or can be stained with fluorescent dyes. In other embodiments, the particles are detected by light scattering. In still other embodiments, the particles comprise another easily detected property, such as conductivity or opacity. In yet a further embodiment, the particles are autofluorescent, or can be stained with fluorescent dyes, and the particles are detected by light scattering and/or conductivity or opacity.

Cell based particles. In some embodiments the particles to be detected are living cells/organisms which are autofluorescent. In the case of the evaluation of cells/organisms without autofluorescence, or previously living, but now-dead cells/organisms, specific fluorescent dyes or dye systems, which are known in the art to stain such cells/organisms, may be useful. In other embodiments, light scattering methods are used to detect cell/organisms. In yet a further embodiment, the particles to be detected are autoflorescent or can be stained with fluorescent dyes and the particles are detected by light scattering and/or conductivity or opacity.

Particle sizes capable of being analyzed by the submersible flow imager will be dictated, at least in part, by the diameter of the core, which comprises the imbibed sample, which flows through the sheath tubing, and the flow cell. The core is surrounded by the sheath fluid while flowing through the sheath. In general, particles will have a smaller (in the shortest dimension) cross-sectional diameter than the cross-sectional diameter of the flow cell. Thus for a cross-sectional diameter of approximately 180 μm, particles of approximately 150 μm or less may be analyzed. Larger particles may be analyzed with larger flow cells (e.g., approximately 360 micron flow diameter enables analysis of cells greater than approximately 150 μm, preferably greater than approximately 200, 250, or 300 μm).

Other suspended particulates, such as detritus, empty diatom frustules, and heterotrophic organisms may also be evaluated in the submersible flow imager.

In one embodiment the submersible flow imager comprises a flow system, a detection system, an electronics system, an antifouling means, and a housing. The flow system is the system by which the particles to be detected are imbibed by the submersible flow imager and then transported through the submersible flow imager, including through the detection path of the detection system. The detection system is the system which detects certain aspects of the sample particles. The electronics system regulates the flow of sample particles through the flow system, the operation of the detection system, and the operation of the antifouling means. The antifouling system attempts to prevent and/or remove the bio-fouling of elements of the submersible flow imager that are subject to bio-fouling. The housing is appropriately waterproof and provides a protective structure around the flow system, detection system, electronics system, and the antifouling system. In one embodiment, the housing is water-tight. In another embodiment, the submersible flow imager comprises multiple housings, with modules of the submersible flow imager being located in separate housings. In another embodiment, the electronics system is located in one housing, and the remaining systems are located in a separate housing. In yet another embodiment, the housing of the submersible flow imager is the payload bay of a vehicle. In yet another embodiment, the vehicle is an unmanned vehicle, such as a glider, auv, or rov.

In an embodiment, the imaging apparatus is constructed around an optical breadboard (e.g with dimensions of 20.32×60.96 cm) comprised of one or more off-the-shelf components. The fluid-handling and electronics components are mounted on opposite sides of the breadboard (FIG. 1). The breadboard hangs from the end cap of the submersible flow imager. The end cap, when secured in place, creates a watertight seal with the housing of the submersible flow imager. In one embodiment, the end cap creates a water tight seal with the housing through the use of two nitrile o-rings. In one embodiment, the end cap comprises connections for transmitting data. In another embodiment, the end cap comprises external connections to an observatory guest port for power and Ethernet communication with the shore or devices capable of receiving such communications, regardless of whether they are located on shore. In yet another embodiment, communication between the electronics system and the connections for transmitting data is effected via cable. In a further embodiment, the communication is approximately 10 megabits/second and is between the observatory guest port and the electronics system. In another embodiment, the cable is a Category-5 cable. In still another embodiment, communication between the submersible flow imager and the shore or devices capable of receiving such communications, regardless of whether they are located on shore, is accomplished using optic fiber.

In one embodiment, the electrical system comprises a power supply. In another embodiment, the power supply comprises 36 V DC (100 W).

The Flow System. The flow system comprises the flow path. The sampled liquid suspension, which comprises particles to be analyzed, travels within the submersible flow imager device, from imbibition through to either disposal or preservation. Any suitable means known in the art may be employed as a flow path (e.g., a tube, hose, or other hollow object that is capable of transporting liquid). In one embodiment, the flow path comprises a tube or hose. The flow path comprises the sheath tubing and the sheath fluid. In many embodiments all or part of the flow path is comprised of materials resistant to fouling. Typical fouling resistant materials include, copper, Teflon, and other hydrophobic materials. In other embodiments the flow path is comprised of materials stable to treatment with the preferred anti-fouling agents such as sodium hypochlorite and surfactants. The flow system further comprises systems for recycling imbibed fluids and the sheath fluid. Functionally, the flow system comprises a minimum of 7 specific subsystems. The subsystems comprise: (i) sample intake means, (ii) pumping means, (iii) particle suspension means, (iv) delivery means, (v) detection path, (vi) detection interface, and (vii) valve control interface. Each subsystem may be present singly or multiply depending on the needs of the specific embodiment.

In one embodiment, the flow system of the apparatus is based on that of a conventional flow cytometer—hydrodynamic focusing of a core, which comprises the sample stream, into the sheath fluid carries the particles to be analyzed in a single file fashion through a laser beam and then through the optical system's field of view. In another embodiment, the flow system is substantially horizontal. In another embodiment, the flow system is substantially vertical. In still another embodiment, part of the flow system is substantially vertical while other parts of the flow system are positioned in a non-vertical orientation.

In one embodiment, the flow system comprises a substantially vertical detection path and a detector interface. In another embodiment, the flow system comprises a substantially horizontal detection path and a detector interface. In one embodiment, portions of the flow path are substantially vertical while other portions of the flow path are in a non-vertical orientation. In another embodiment, portions of the flow path are substantially vertical while other portions of the flow path are substantially horizontal. In accordance with one embodiment of the flow system, the flow system further comprises a non-vertical delivery means. In an embodiment, the submersible flow imager is substantially horizontal while being towed and substantially vertical while at rest. In a further embodiment, whether the submersible flow imager is substantially horizontal or substantially vertical depends on the speed at which the submersible imager is travelling, either by being towed or while mounted to a vessel, vehicle, or platform. Additionally, the electronics system may be substantially, spatially removed from the flow system. In accordance with other embodiments, the device also comprises at least one of the following: a particle staining system, a particle sorting system, and/or a particle concentrating system.

In one embodiment, a sample is injected into the center of a sheath within the flow path. The sample can be any appropriately sized particles in suspension, including, but not limited to, blood, sediment in water, lake water, fresh water, marsh water, and sea water. In an embodiment, the sample comprises seawater. The sheath tubing can be made of any material that is known in the art, such as plastic, polymers, metal, etc. The sheath comprises a flow of sheath fluid, which is particle-free. In one embodiment, the sheath fluid is water. The injection of the sample into the sheath results in the sample core being confined to the center of the flow of the sheath fluid, with the sheath fluid substantially creating a "collar" around the sample. Surrounding the sample with the sheath fluid results in the sample, and thus the particles to be analyzed, being substantially confined to the center of the flow cell in the detection system, and helps ensure that the particles to be analyzed are in focus as they pass through the optical system, which is part of the detection system. In one embodiment, the sheath fluid is recycled through a filter cartridge, which removes particles after they have been analyzed by the detection system. The removal of the particles after analysis allows for the efficient use of antifouling agents, which help the system operate for longer periods of time without the need for maintenance or cleaning. In one embodiment, the use of antifouling agents results in the submersible flow imager being capable of being used for at least 6 months without maintenance.

In one embodiment, the flow system's operation comprises the sheath fluid and the sample to be analyzed (which in one embodiment is seawater comprising particles) are forced through a pair of 0.2 µm filter cartridges (e.g., Supor; Pall Corp.) by a gear pump (Micropump, Inc. Model 188 with PEEK gears) and flow through a conical chamber to a quartz flow cell.

The Sample Intake Means. The sample intake means imbibes a sample from the aquatic environment and delivers it, via the pumping means, to the delivery means. Any suitable means known in the art may be employed as a sample intake means. In one embodiment the sample intake means subsystem comprises an open tube and inline filter. The sample intake means subsystem should be designed such that it prevents imbibition of particles larger than the flow cell channel and does not damage fragile cells or colonies that the sample intake means subsystem imbibes.

The sample intake means subsystem should not detrimentally introduce air bubbles or produce flow shear likely to damage fragile cells or colonies.

The Pumping Means. The pumping means subsystem provides the motive force for imbibition of a liquid from the environment and transfer of the imbibed sample through the flow system. Any suitable means known in the art may be employed as a pumping means (e.g., a peristaltic pump, positive displacement pump, or negative displacement pump, etc.) and may function through the use of positive or negative pressure. In one embodiment, the pumping means comprises a syringe pump.

The Particle Suspension Means. In some embodiments, the flow rate of the sample through the flow path is low (e.g., approximately 0.1 to 1 ml/min). Therefore, one feature of the submersible flow imager is that the imbibed particulates pass through the system without settling out before reaching the detector. In embodiments that comprise fully vertical configurations, particle settling is not generally a concern since the flow is downward through a straight flow path. In such case, the particle suspension means subsystem is considered to be the liquid of the imbibed sample itself. However, in embodiments that any aspect of the flow system being located in a non-vertical orientation, particle settling may be a significant issue. Embodiments where any portion of the flow system is located in non-vertical orientation include, but are not limited to, low relief embodiments where the detection path may be in a different orientation than the delivery means. In embodiments where any one or more element of the flow system is in a non-vertical orientation, to ensure the particle suspension remains substantially intact, the continued suspension of the particles is ensured through exposure of the sample to turbulent flow or by moving particles at a velocity high enough to ensure that the particles do not settle while in the flow path. In one embodiment, the use of a syringe pump may itself be adequate to impart turbulence and/or the necessary velocity, when one or more element of the flow system is in a non-vertical orientation, to prevent particles from settling. In an alternative embodiment, a mixing device, including but not limited to a magnetic stirring bar, may be placed within the flow path at points of low velocity. In an embodiment, the magnetic stirring bar is located in the barrel of the syringe. In embodiments with a magnetic stirring bar, the magnetic stirring bar may be moved by an external magnet connected to a motor or solenoid. The presence of a mixing device, such as a magnetic stirring bar, within the syringe may preclude complete injection of the sample volume, but this is unimportant if the sample is well mixed. In yet another embodiment, the particle suspension means comprises a syringe pump and a magnetic stirring bar. In yet another embodiment, the particle suspension means comprises rotation of the syringe about its axis of movement. In other embodiments, particle suspension means comprises the tubing/piping/etc., which comprises the flow path, having a cork-screw shape. In a further embodiment, the wave action of the body of water in which the submersible flow imager is located comprises the particle suspension means. The particle suspension means can comprise any device or method that is known in the art for maintaining particles in suspension, whether through imparting turbulence into the sheath fluid containing the particles in suspension or otherwise.

In still another embodiment, the particle suspension means comprises the addition of a liquid to mix with the sample, to assure particle suspension. The liquid to be mixed with the sample can be any liquid that causes the suspended particles to be closer to neutral density (to float) than in its absence. Non-limiting examples of suitable liquids to be mixed with the sample include high-viscosity, hydrophilic liquids, such as: glycerol, isotonic sugars, polyethylene glycols, and other neutral surfactants. In some embodiments, the particle suspension means is a viscous suspending medium. In other embodiments, the viscous suspending medium that comprises the particle suspension means can also be used to carry the staining medium.

The Delivery Means. The delivery means subsystem comprises the portion of the flow path connecting the pumping and/or the particle suspension means to the detection path. In some embodiments of the submersible flow imager where all aspects of the submersible flow imager are substantially vertical, the exit port of the pumping means comprises the delivery means. In other embodiments, where at least one element of the flow system is in a non-vertical orientation, portions of the flow path are non-vertical, and may occur at any suitable orientation relative to the detection path, which is substantially vertical. In these embodiments, the tubing/piping/etc. which comprises the flow path will have a directional change prior to connecting to the detection path. In some embodiments, the delivery means are designed so that, in combination with the particle suspension means, the particles to be analyzed do not settle out of the flow path.

The Detection System. The detection subsystem comprises the detection path, which comprises the portion of the flow path which carries the suspended particles into the detection interface subsystem. The detection interface subsystem comprises the core. The detection system also comprises the optical system and the sorting system. In one embodiment, the detection path and detection interface are substantially oriented vertically (e.g., in the direction of gravity), with a flow path contiguous with the delivery means and comprises the detection system. In other embodiments, the detection path and the detection interface are positioned in a non-vertical orientation. In yet another embodiment, the detection path and the detection interface are substantially horizontal.

The detection interface subsystem comprises the core, the sheath, and a flow cell. In one embodiment, the flow cell is a light transmitting flow cell. The light transmitting flow cell may be made of quartz, glass, or plastic, depending on the means of detection and the aspects of the sample particles that are being detected.

In operation the sample particle suspension is injected into the detection path by injecting, via the deliver means, the sample particle suspension into a flowing particulate-free sheath fluid. In some embodiments, in order to ensure the suspended particles to be sampled remain concentrated within the center of the sheath flow and pass through the flow cell in a correct orientation, the detection path and detection interface subsystem are maintained substantially vertically and fluids move through the detection path from top to bottom (with the flow of gravity). In other embodiments, the detection path and the detection interface subsystem are positioned in a non-vertical orientation. In a further embodiment, the detection path and the detection interface subsystem are positioned so that they are in a substantially horizontal orientation. While moving within the detection path, the particles are exposed to the detection means. In some embodiments, the detection means includes exposure to an excitation wave length to stimulate the emission of light in the presence of an appropriate detector. In other embodiments, alternative detection means and systems besides fluorescence may be employed. Alternative detection means and systems that may be used include, but are not limited to, light scattering detection, conductivity detection, and any other detection system which is known in the art. The detection means include, but are not limited to, lasers, LEDs, or other focused light sources.

Sheath flow within the flow path is established through the use of the sheath fluid, which may be continuously recycled and reused or discarded after exiting the flow path, depending on the specific needs of the application as described elsewhere herein. In one embodiment, the sheath fluid is continuously recycled and reused. In another embodiment, the sheath fluid is discarded after exiting the detection path. In another embodiment, the sheath fluid is discarded after exiting the sorting system. In yet another embodiment, the sheath fluid is continuously recycled except when the sheath fluid contains a stain, which is added by the detection system. The flow cell comprises a channel. The core, which is surrounded by the sheath fluid, flows into the flow cell. In one embodiment, the flow cell channel is modified from that of the BD FACSCalibur flow cell to produce a wider ribbon-shaped core, thus increasing the sample volume that can be processed without increasing the core thickness. The submersible flow imager comprises at least two solenoid valves. The first solenoid valve is located between the exit from the flow cell and the entrance to the sheath filter. The second solenoid valve is located at a penetration point through the underwater housing of the submersible flow imager. The purpose of the second solenoid valve is to provide a source of seawater for new, as opposed to recirculated, sheath fluid (see Example 2—Detection of Stained Phytoplankton).

The detection system detects one or more aspects or features of the suspended particles passing through the detection interface subsystem of the flow system. In some embodiments, the sample particles comprise a fluorescent aspect, either inherently or after being exposed to a dye capable of causing part or all of the particle to fluoresce. Any detectable feature of the particles may be detected through use of an appropriate detection means, which are known in the art. In one embodiment, the detection system comprises a device to detect fluorescence. The detection system interfaces with the detection path subsystem and the detection interface subsystem. In one embodiment, the flow cell comprises a light transmitting flow cell.

The detection system further comprises a combination of video and flow cytometric technology, which comprises the optical system, to both capture images of organisms for identification and measure chlorophyll fluorescence associated with each image. In one embodiment, images can be automatically classified with software based on a support vector machine, while the measurements of chlorophyll fluorescence allow the efficient analysis of phytoplankton cells by triggering on chlorophyll-containing particles. In an embodiment, quantitation of chlorophyll fluorescence in large phytoplankton cells enables the discrimination of heterotrophic and phototrophic cells.

Electronics System. The detection system and flow systems are electronically controlled by an electronics system that comprises: controllers, a data acquisition device, a power source, and a data processor. In one embodiment, the electronics system also comprises telemetry devices. In one embodiment, the electronics system also controls the antifouling means.

In another embodiment the electrical system comprises programmable operations. In another embodiment, the programmable operations comprise at least one of the following: data acquisition, transfer of data (to shore or to any other device capable of receiving data, whether located on shore or not), adjustment of sampling frequency, adjustment of rate of sample injection, injection of internal standard beads, flushing the flow cell with an anti-fouling or cleaning agent, flushing the sample tubing with the cleaning agent, flushing the sheath with cleaning agent, backflushing the sample tubing to remove potential clogs, flushing the flow cell to remove air bubbles, adding antifouling agents to the sheath reservoir to prevent biofouling of the internal surfaces of the submersible flow imager, focusing the optical system, or focusing of the imaging objective lens (or lenses).

Antifouling Means. All instruments exposed to the aquatic environments are subject to bio-fouling. This problem can be acute for optical sensors since biofilms and macro-organisms can interfere with light transmission and can ultimately render sensing modalities ineffective. Biofouling can also obstruct or contaminate sample particle intake. In one embodiment, the submersible flow imager prevents bio-fouling of intake and internal surfaces through a multi-pronged approach. First, the flow cell is protected from contact with seawater by containing the sample within the sheath fluid. Further, the sheath fluid is treated so that it remains particle free. In one embodiment, the sheath fluid is treated by recirculation of the sheath fluid through particle filters. In another embodiment, the sheath fluid is treated by regular injection of a biocide. In yet another embodiment, the sheath fluid is treated by recirculation of the sheath fluid through particle filters and regular injection of a biocide. In another embodiment, the sample particle intake and the internal tubing of the submersible flow imager are subject to automated periodic cleaning cycles, accomplished by backflushing with appropriate cleaning agent. Typical cleaning agents include acids, bases or surfactants. In one embodiment the cleaning agent is sodium hypchlorite.

Use of the Submersible Flow Imager. Generally, a sample (e.g., seawater) comprising a liquid suspension of particles is injected into the center of a sheath flow of particle-free water; all the particles are thus substantially confined into a core flowing through the center of the flow cell, which ensures that each particle is in focus as it passes through the detection system, which comprises the optical system. In an embodiment, the sheath fluid is recycled through a filter cartridge, which removes the sample particles after they have been analyzed. Recycling the sheath fluid and removing the sample particles after analysis allows for the efficient use of antifouling agents so the system can operate for months at a time without the need for maintenance or cleaning.

In one embodiment, the submersible flow imager is contained in a watertight housing. In one embodiment, the submersible flow imager is operated continuously and autonomously, under the direction of a computer whose programming can be modified by a remote operator. In such embodiments, programmable operations include but are not limited to: data acquisition, data transfer to shore or to a device capable of receiving such data transmission regardless of whether the device is located on shore, activating and/or controlling motors, activating and/or controlling valves, adjustment of sampling frequency, adjusting rate of injection of samples, injection of internal standard beads, flushing the flow cell and/or sample tubing with detergent, backflushing the sample tubing to remove potential clogs, adding biocide to the sheath reservoir to prevent biofouling of the internal surfaces, focusing the imaging objective lens, providing dye and/or other additives, recycling of sheath fluids, and similar control activities.

Flow Rate. In one embodiment, flow rates of sample particles through the submersible flow imager range from approximately 0.1 ml/min to approximately 1 ml/min.

Bubble Removal and/or Supression. Under most circumstances, the presence of bubbles within the flow system is undesirable because it disrupts the flow pattern within the flow cell, causing some cells to fail to trigger the detection system or be out of focus. In one embodiment, the submersible flow imager comprises a system to minimize the introduction of bubbles or the generation of bubbles within the imbibed samples and to remove bubbles from the flow cell. In one embodiment, the bubble minimization system comprises regulation of the sample aspiration rate. In another embodiment, the bubble minimization system comprises capabilities for aspiration from above the flow cell and the expulsion of the resulting fluid to the outside of the instrument. In another embodiment a modified vacuum aspirator is used to generate a vacuum while the vehicle comprising the submersible flow imager is in motion. A vacuum so generated is used to draw dissolved air from the imbibed sample in order to reduce the possibility of bubble formation.

Robotic Staining and Imaging.

Use of Stains. In one embodiment, the detection system of the submersible flow imager comprises equipment for the automated introduction of liquid or dissolved stains for the purpose of treating sample particles to enhance the analysis capabilities of the detection system following the detection of the degree of staining of the sample particles by the detection system. The stain utilized should be a stain that will remain stable within the stain reservoir until used. Additionally, the stain used should be a stain that is used in sufficiently small amounts to ensure the capability of the submersible flow imager to stain many samples on long deployments. In some embodiments, the volume of stain used per sample is approximately 10 to 20 µL and the stain reservoir contains approximately 100 to 200 mL, so that the number of samples that can be stained is approximately 5,000 to 20,000 (or approximately 69 to 278 days of continuous analysis at a rate of approximately 0.25 mL of seawater/min.).

Liquid or dissolved stain is introduced from a stain reservoir into the mixing chamber section of the delivery means flow path through the use of a solenoid activated micropump.

In one embodiment, when a stain is used, the sheath fluid will be discarded after a single passage through the detection path. However, in other embodiments, the optional control of sheath fluid recycling is accomplished through the use of two solenoid activated valves (see Example 2—Detection of Stained Phytoplankton) as disclosed above. In some embodiments, the submersible flow imager further comprises a variable filter in the detector portion of the detection system to change the wavelengths of light being detected. The variable filter may comprise one or more filters of variable wavelengths capable of being placed into the detection light path through the use of a motor or solenoid.

Fluorescent Staining Systems. In another embodiment, the detection system comprises a fluorescent staining system. Many fluorescent staining systems, which are known in the art, may be used depending upon the specific needs of the application. Stains may be selected and used by employing principles similar to those of the LIVE/DEAD® products provided by Life Technologies (3175 Staley Road, Grand Island, N.Y. 14072). Non-limiting examples of potentially useful Life Technology stains include:

(i) membrane-permeant calcein AM, which is cleaved by esterases in live cells to yield cytoplasmic green fluorescence, (ii) membrane-impermeant ethidium homodimer-1, which can be used to label nucleic acids of membrane-compromised cells with red fluorescence, (iii) DiOC18(3), which is a green-fluorescent membrane stain that is used to stain target cells prior to exposing the target cells to propidium iodide, (iv) SYBR® 14 nucleic acid stain, which labels live cells with green fluorescence, (v) membrane-impermeant propidium iodide, which labels the nucleic acids of membrane-compromised cells with red fluorescence, (vi) C12-resazurin, which is reduced to red-fluorescent C12-resorufin in metabolically active cells, (vii) SYTOX® Green dye, which is a cell-impermeant green-fluorescent nucleic acid stain, and which can be used to stain cells with compromised plasma membranes (usually late apoptotic and necrotic cells); in this assay, dead cells emit mostly green fluorescence and healthy, metabolically active cells emit mostly red fluorescence; injured cells exhibit reduced red and green fluorescence, (viii) Hoechst nucleic acid stain, (ix) Fluorescein diacetate, which stains cells with intact membranes and esterase activity, and (x) LysoTracker Green, which stains cells with acidic vacuoles.

Low Relief Configuration

Design. In another embodiment, the submersible flow imager is fabricated according to a modularized design, employing the inventive detection path in a substantially vertical orientation with the remainder of the device positioned substantially lateral to the substantially vertical detection path and lower than the top of the detection path; In other embodiments, all aspects of the submersible flow imager, including the detection path, are in a substantially horizontal orientation. Both embodiments are referred to as low relief embodiments. In embodiments where the detection path is substantially vertical, the overall height of the submersible flow imager is primarily dictated by the height of the detection path and any clearance required for the attachment of the delivery path and the device housing. Such configurations can result in a maximum device height of approximately 36 cm or less. In some embodiments, the maximum device height is less than approximately 25, 20, 19, 17, or 15 cm. In alternative embodiments, the laterally positioned systems may extend above and/or beyond the upper reaches of the detector flow path, but below the height required if the entire flow path was disposed in-line and substantially vertical.

In a specific embodiment, the submersible flow imager is configured for low relief (also referred to herein as "IFCB-LR") for operation on platforms and vehicles with instrument height restrictions. One example of such a platform/vehicle is the Wave Glider 3, whose payload bay's dimensions are approximately 59 cm×38 cm×19 cm high. Accordingly, in one embodiment, the submersible flow imager height is no more than approximately 17 cm.

In one embodiment, the submersible flow imager's flow cell should remain substantially vertically oriented (with flow downward) so that the sinking of particles as they flow through the detection system does not affect their trajectory (and hence signal detection and image focus). The flow cell assembly in the submersible flow imager is approximately 17 cm tall, so use of the flow assembly is compatible with installation of the submersible flow imager in a Wave Glider 3 payload bay. In another embodiment, the submersible flow imager's flow cell should remain substantially horizontally oriented and the sinking of particles is prevented through the use of the particle suspension means.

In one embodiment, the design of the submersible flow imager comprises the sample syringe pump being located substantially vertically above the flow cell. In some embodiments, the syringe pump is approximately 30 cm in length, therefore locating the sample syringe pump substantially vertically above the flow cell is not well suited for most small vehicles and platforms. When the submersible flow imager is to be deployed in a small vehicle or platform, the syringe pump may be positioned substantially horizontal to the flow cell or replaced by a different method of injecting sample water.

In one embodiment, the optical system of the detection system comprises a trigger laser, an illumination system, and a detector system. The illumination system comprises a flash lamp and a condenser. In a further embodiment, the illumination system comprises a Xenon flash lamp. The detector system comprises an objective lens, photomultiplier, and a camera. The optical components of the optical system occupy a space of approximately 40×16×9 cm, which will fit in the Wave Glider 3 payload bay. In order to meet this space restriction, the image as shown in FIG. 1 must be re-oriented from vertical to horizontal. In another embodiment, the electronics module, which occupies a space of approximately 13×13×12 cm, and the fluidics module, which occupies a space of approximately 16×12×12 cm, are relocated to meet the space limitations of the Wave Glider 3 payload bay. In an alternate embodiment, in situations where payload space is available in fixed size bays, some of the modules can be located in separate bays other than the bay in which the optical components are located. In yet another embodiment, if the vehicle or platform has integrated processors and/or data storage capacity, the electronics module can be further subdivided to offload these functions from the instrument to the platform.

Sorting System.

Image-Based Cell Sorting and Preservation. The detection system further comprises a sorting system. Flow cytometric cell sorting, using fluorescence and light scattering to classify cells to broad groups, has become a powerful tool for microbial ecologists, especially in the context of advances in genomic methods. The ability to sort with genus or species resolution would be even more powerful; for example, species-sorted samples from different stages of a bloom would provide unprecedented opportunities for transcriptomic studies to provide a direct link between species and gene expression as a function of environmental condition. To date, these methods have not generally been available for analysis while at sea.

A prototype imaged-based cell sorter function has been incorporated into a submersible flow imager. The major challenge in this approach is that the speed of image-based sorting is fundamentally limited by that of image processing and classification computations. Currently, image processing cannot be completed in the fraction of a second available between a sample particle's passage through the detection region and the sorting location. Accordingly, in one embodiment, the submersible flow imager comprises a two-step sorting procedure. The first step comprises the use of a commercially available BD FACSCalibur sort flow cell assembly, in which a 'catcher tube' is positioned below the flow cell. At rest, the catcher tube opening is located outside the core, with the particle-free sheath flowing through it. When a sample particle with the desired fluorescence and/or light scattering signature is detected, a piezo element pushes the catcher tube out into the core, so that the catcher tube will be able to collect the particle at the correct moment after the particle leaves the flow cell and the sample particle of interest goes into the tube. The second step comprises classifying the captured image. In this embodiment, the imaging sorter comprises a miniature solenoid valve. In the imaging sorter, a miniature solenoid valve, which is located below the catcher tube, shuts off the flow after the cell is captured and the sample particle then waits in the catcher tube while the image is classified. If the image does not match pre-determined target criteria, the sample particle is sent to the waste stream and the sorting process starts over. If the image classification does satisfy the target criteria, a separate solenoid directs the flow to a capillary above a well plate. A second laser and detector are used to verify that a sample particle was actually captured and to enable the correctly timed release of a drop the sheath fluid containing the sample particle to be preserved into the well.

In one embodiment, fluorescence measurements and image capture takes place in a BD FACSCalibur sort flow cell. In another embodiment, the catcher tube is controlled by FACSCalibur circuitry (not shown). In yet another embodiment, the solenoids, capillary fluorescence detector, waste catcher (for removing the sheath flow in between sorted cells), and the well plate X-Y translator are controlled by a PIC microprocessor (not shown).

The 2-step image-based sorting system described above is functional, but slow, because the sorting decision depends on computationally intensive image processing and classification algorithms which can require up to several seconds, depending on the image size. During the time the sorting decision is occurring, no other sample particles can be processed. Additionally, in the 2-step process described above, the sorted drops are exposed to the air and only a single plate of samples can be sorted, neither of which is optimal for operation in situ. Finally, in the 2-step imaging-based sorting process described above, a relatively large volume of seawater (approximately 1 ml) accompanies each sorted particle, making it difficult to manually check sorting efficiency. Further, the relatively large volume of seawater that accompanies each sorted particle can cause interference problems in molecular assays. Accordingly, in another embodiment, the second stage of the sorting process uses an alternate strategy. In this embodiment, the second stage of the sorting process is based on methods that allow for parallel rather than serial processing of sample particles.

Figure 6:
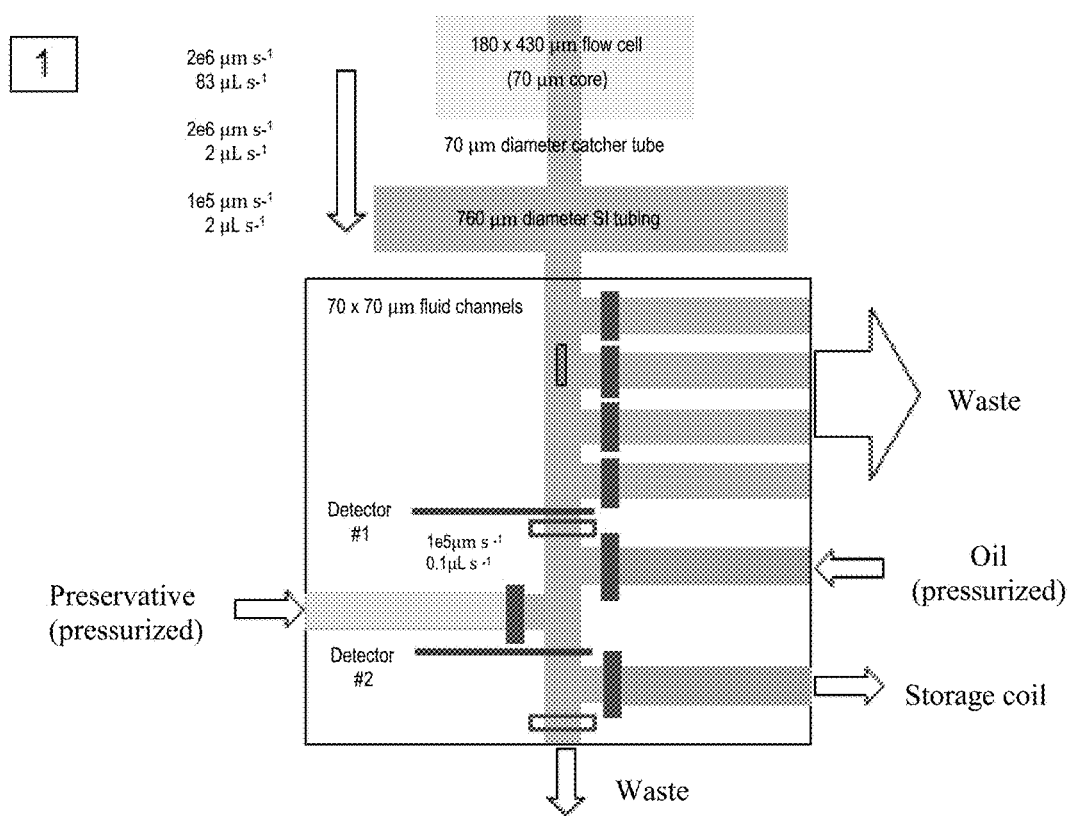
FIG. 6 is a chart depicting the process for microfluidic injection of sorted cells into storage tubes.
Figure 7:
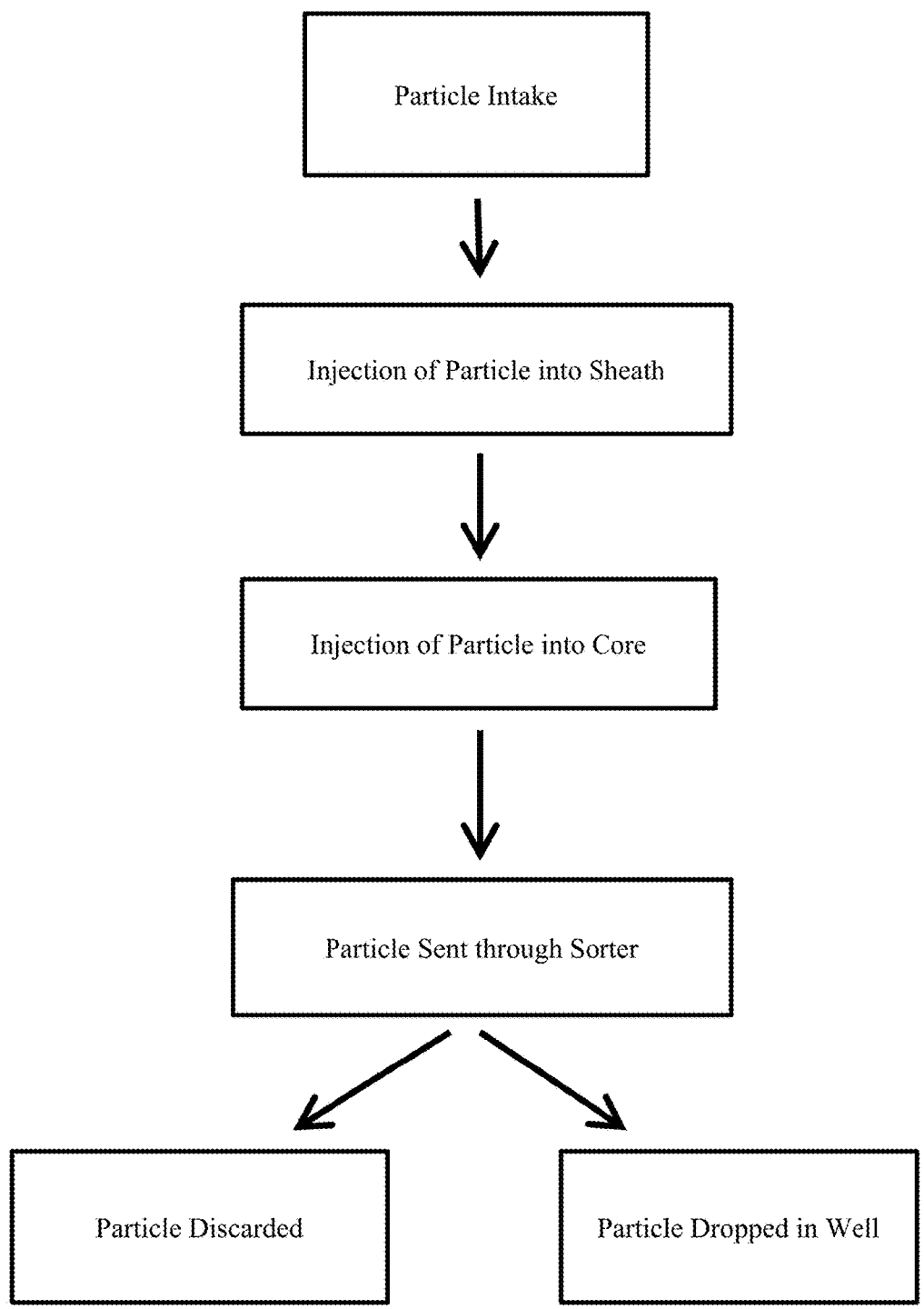
FIG. 7 is a diagram of the flow path of one embodiment of the submersible flow imager.
Figure 8:
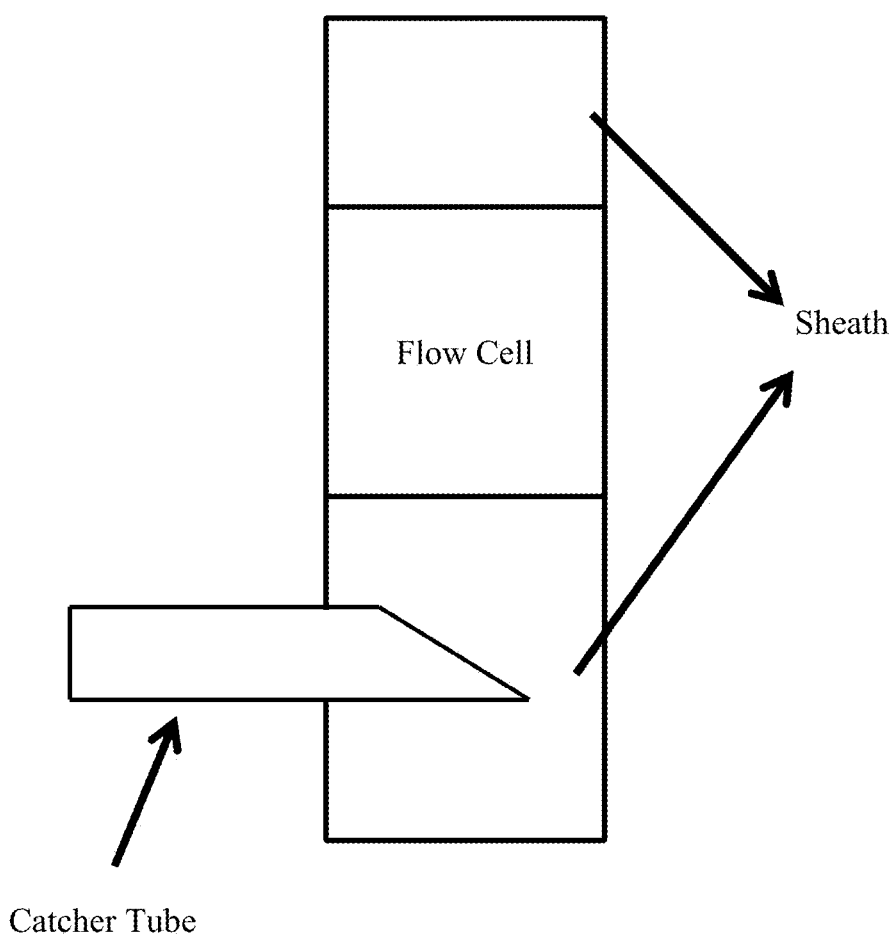
FIG. 8 is depicts embodiments of the invention where a catcher tube is employed as part of the sorting system.
Figure 9:
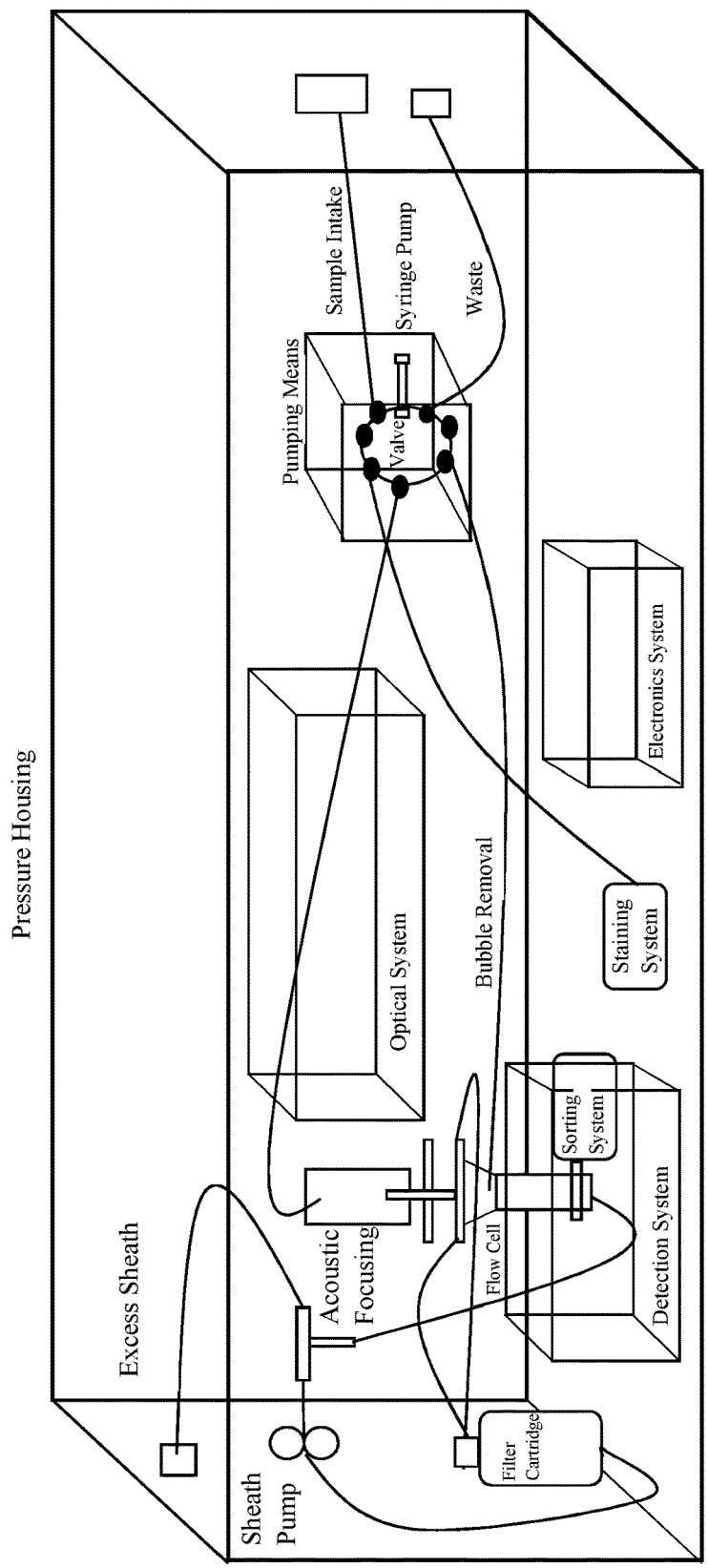
FIG. 9 depicts embodiments of the invention showing components separated into modules.

In this alternate embodiment where the second stage of the sorting process enables parallel processing, the second stage of the image-based sorter is replaced by a sorted drop storage module (see FIG. 6), which allows the fluorescence-based and image-based sorting steps to be separated in time. In this embodiment, every potential target, e.g., those sample particles with high-fluorescence, scattering, and/or long signal duration, etc., is captured by the real-time sorting step, which was step one, and stored, so that more specific image-based sorting can be carried out in a separate procedure later (after image analysis, classification, and identification of target groups). In one embodiment, the storage of sorted particle samples, that are retained from the first step (as well as the subsequent image-based sorting), is carried out using water-in-oil technology in which stable fluid compartments are formed and manipulated, each fluid compartment containing a sorted sample particle. Each sorted sample particle from the initial sorting step is injected, along with a small parcel of water, into an oil stream in a microfluidic channel, to form a stable chain of water segments, each water segment being separated from other water segments by oil, whose contents are knowable from the corresponding saved images. The water segments can be stored in a compact coil of tubing for an extended period of time, during which time the image processing and classification can be completed. In another embodiment, the storage of sorted particle samples, that are retained from the first step (as well as the subsequent image-based sorting), is carried out using a reel of tape with micro-wells, where each well is sealed containing a fluid drop and associated sorted sample particle. These steps are carried out in the instrument deployed in the field. Later, back in the shore laboratory, the desired water segments are retrieved from the coil of tubing or reel of micro-well tape, allowing specific target groups to be isolated, as desired. In this embodiment, the image-based sorter prototype utilizes a second stage capillary detection system, whose function is to verify that the preliminary sort captured a sample particle and then time that sample particle's release into a well. This capillary detection system is the "front end" of the emulsion system of cell sorting. In one embodiment, the microfluidics system processes drops more rapidly than the camera's maximum frame rate, which is 30 Hz, so the emulsion based sorting system is capable of sorting sample particles based on their images at rates that are essentially the same as those of analytical sampling.

In one embodiment, the oil and water segments are stored in coiled tubing. In another embodiment, for transcriptomic analysis, the sample stream is mixed with the RNA preservative (e.g. ethanol). The RNA preservative can be any substance that is now known or in the future determined to preserve RNA. Later before the injection of the sample along with the small parcel of water into the oil stream to preserve RNA. In this embodiment, the storage chamber temperature can be controlled, if necessary.

The submersible flow imager's sampling rate is limited as a consequence of the stringent requirements of the imaging that enables the resolution of cells to the genus or species level because the depth of the focus of the microscope objective is only approximately a few microns. In one embodiment, the sample stream is hydrodynamically focused to form a ribbon-shaped core, but to achieve a core this thin the sample flow rate is limited to approximately 0.25 mL/min. This sampling rate is 5 times faster than that of the FCB, which measures *Synechococcus* integrated optical properties, but the difference in cell concentration between *Synechococcus* and large diatoms is typically far more than 5-fold, even when the diatom biomass far outweighs that of the picoplankton; *Synechococcus* typically occurs at approximately $10^4$-$10^5$ cells/mL, while all the diatom species combined often comprise only approximately $10^3$ cells/mL.

Similar sampling limitations apply to many methods in plankton ecology. In the case of the submersible flow imager, simply pumping samples faster degrades the quality of the images because the thickness of the sample core in the flow cell is determined by the relative rates of sample flow and sheath flow; therefore, if the core gets thicker, some cells will no longer be at the proper distance from the microscope objective. However, increasing the sheath flow to correct the core thickness causes the velocity to increase, which results in blurred images.

An alternative to increasing the instrument's sampling rate is to pre-concentrate samples by removing most of the water from the sample, leaving the sample particles behind. Pre-concentration by settling, centrifugation, or filtration is a routine part of land-based microscopic or bulk constituent analysis. Settling and centrifugation are not optimal for in situ operations. Filtration is only semi-quantitative when the samples need to be re-suspended for analysis, as sample particles or cells can be destroyed and/or stick to the filter. In one embodiment, the submersible flow imager detection system further comprises filtration for pre-concentration. Alternatively, acoustic standing waves can be a solution for in-line concentration of flowing samples. Accordingly, in an alternate embodiment, the delivery system comprises acoustic focusing devices that create acoustic standing waves for in-line concentration of flowing samples. In yet another embodiment, the acoustic focusing device comprises a piezo electric drive.

Though acoustic focusing devices can take several forms, among the simplest is a piezo electric drive that generates a standing wave in a rigid cylindrical tube. As the standing wave in this case is generated by the tube, it has a complex structure that leads to a single pressure node that radially focuses particles to the center of capillary flow. This approach has been applied to land-based flow cytometry, where tests with plastic beads and mammalian cells demonstrated that an acoustic system can achieve particle focusing comparable to that of a conventional hydrodynamic system, and the system has been incorporated into a commercial flow cytometer (Attune, Applied Biosystems).

Figure 2:
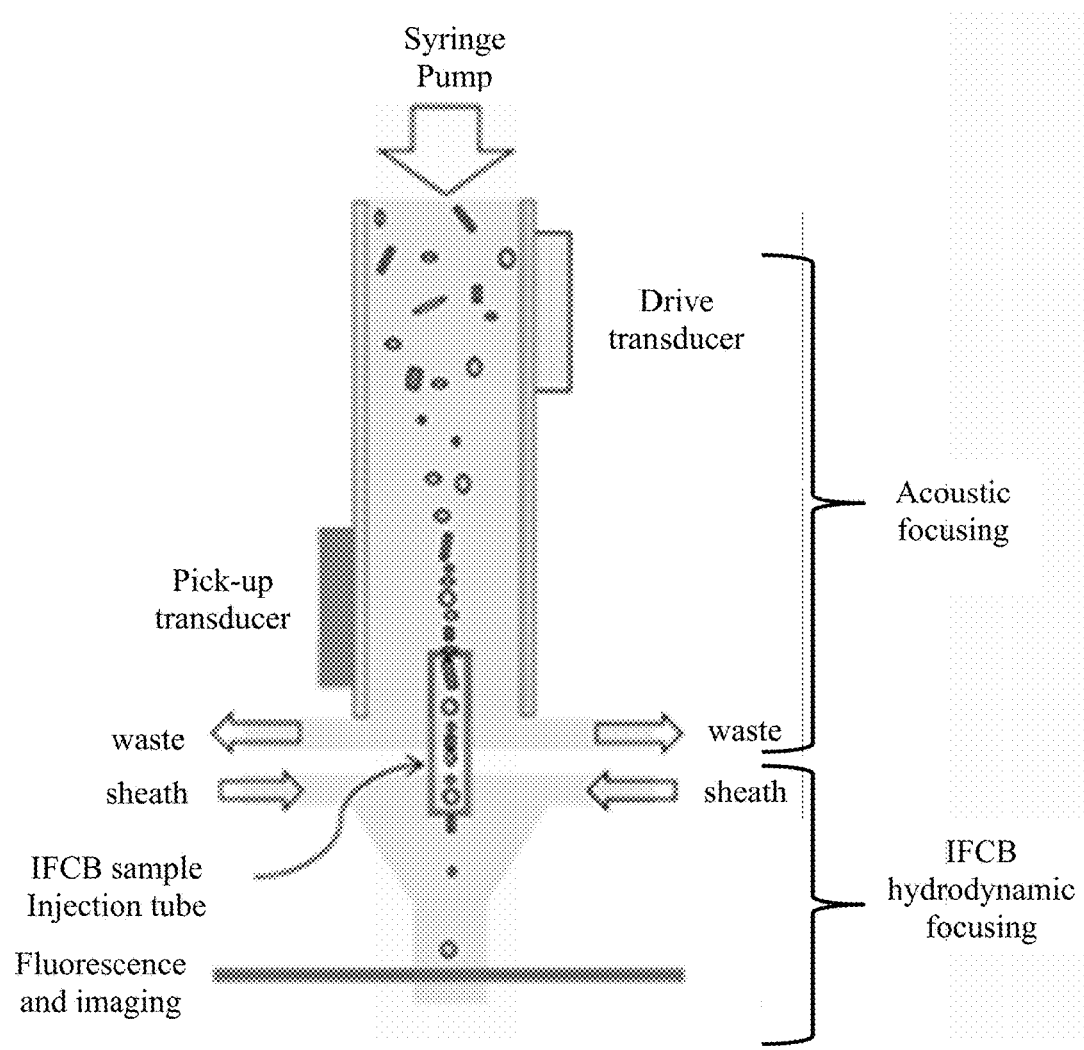
FIG. 2 is a depiction of acoustic focusing elements of one embodiment of the submersible flow imager. The drive transducer on the focusing tube sets up the acoustic standing wave, and the pick-up transducer monitors its frequency for use in feedback regulation. The focused particles at the end of the tube enter the submersible flow imager's existing flow and detection system.

In one embodiment, the submersible flow imager further comprises an acoustic focusing element, located just prior to the flow cell, to increase its sampling rate (FIG. 2). In this embodiment, the submersible flow imager's hydrodynamic focusing system is retained because it prevents biofouling and because it maximizes the in-focus sample volume by creating a ribbon-shaped core flow. The sampling syringe pump pushes seawater at approximately 4 mL/min through an approximately 2-mm internal diameter (also referred to as "ID") tube, which is approximately 190 mm long and equipped with an acoustic transducer. At the outflow end of the tube, all the particles are in approximately the center 40 μm of the flow; this part of the flow enters the submersible flow imager's sample injection needle (ID approximately 380 μm), with the remainder of the flow sent overboard. Since the submersible flow imager's current sample rate is approximately 0.25 mL/min, the modification represented in this embodiment is an approximate 16-fold increase in sample rate. In other embodiments, even higher concentrations of sample particles can be achieved by increasing the cross-sectional diameters of the acoustic focusing channel.

For scientific purposes where the current data density is already sufficient, increasing the sampling rate is still advantageous because it allows for a decreased duty cycle, which is important for power conservation during moored deployments. If power is not a consideration, the faster instrument is able to complement standard sampling with alternative functions, such as cell sorting or specialized measurements with fluorescent probes. Increased sample particle concentration also allows for reduced velocity of the sheath flow, allowing longer-duration camera exposures, which in turn allows for replacement of the Xenon flash lamp in the illumination system by a less powerful LED light source, thereby reducing space, power, and expense. Accordingly in one embodiment, the illuminating system further comprises a LED light source. In yet another embodiment, the illuminating system comprises a pulsed laser.

Applications. Useful applications for the submersible flow imager include: (1) detection of fluorescent or fluorescent-stainable toxins or chemicals taken up by the sample particle; (2) detection of intracellular calcium levels within sample particles using calcium sensitive dyes; (3) assessment of the metabolic state of specific sample particles; (4) detection of NAD/NADH content of sample particles; (5) species identification; and (6) the presence of chlorophyll.

EXAMPLES

Example 1

Fully Vertical Flow Analyzer

In one embodiment, the flow system of the submersible flow imager is based on that of a conventional flow cytometer and comprises hydrodynamic focusing of a seawater sample stream in a particle-free sheath flow that carries cells in a single-file manner through a laser beam and then through to the camera's field of view.

In this embodiment, sheath fluid, plus the suspended sample, flows through a conical chamber to a quartz flow cell. The flow cell housing and sample injection tube is from a Becton Dickinson FACScan flow cytometer, but the flow cell is replaced by a custom cell with a wider channel. The channel dimensions of the custom flow cell are approximately 800×180 μm (Hellma Cells, Inc.). Since the FACScan objective lens housing, which normally supports the plastic flow cell assembly, is not used, an aluminum plate that is approximately 3.175 mm thick is bolted to the assembly. The aluminum plate is used to support the flow cell assembly. The sheath fluid is recycled by using a gear pump (Micropump, Inc. Model 188 with PEEK gears) to force the sheath fluid through a pair of approximately 0.2 μm filter cartridges (Supor; Pall Corp.), one of which is positioned before the flow cell and the other after the flow cell.

The sample is imbibed through an approximately 130 μm Nitex screen, which prevents flow cell clogging. The Nitex screen is protected against biofouling by an approximately 1 mm copper mesh. After the sample is imbibed through the Nitrex screen, the sample is injected through a stainless steel tube (approximately 1.651 mm OD, approximately 0.8382 mm internal diameter; Small Parts, Inc.) into the center of the sheath flow in the cone above the flow cell by a programmable syringe pump (Versapump 6 with approximately 48,000 step resolution, using a 5-mL syringe with Special-K plunger; Kloehn, Inc.). The tubing is of PEEK material (approximately 3.175 mm internal diameter for sheath tubes, approximately 1.588 mm for others; Upchurch Scientific).

An 8-port ceramic distribution valve (Kloehn, Inc.) allows the syringe pump to carry out several functions in addition to seawater sampling. These include regular (approximately daily) addition of biocide to the sheath fluid to prevent biofouling, and regular (approximately daily) analyses of beads (approximately 20 μm or approximately 9 μm red-fluorescing beads, Duke Scientific, Inc.) as internal standards to monitor instrument performance. In addition, the sample tubing, which is not protected from biofouling by contact with biocide-containing sheath fluid, is treated with detergent (approximately 5% Contrad/1% Tegazyme mixture) during bead analyses (approximately 20 min/day) to remove fouling. Finally, the syringe pump is used to prevent accumulation of air bubbles in the flow cell, which may result from the degassing of seawater, since air bubbles could disrupt the laminar flow pattern. Before each sample is injected, sheath fluid is withdrawn from the sample injection needle and from the conical region above the flow cell, and discarded to waste. The biocide solution, suspended beads, and detergent mixtures are stored in separate 100-mL plastic bags with Luer fittings (Stedim Biosystems).

In one embodiment, flow cytometric measurements are derived from a red diode laser (SPMT, 635 nm, 12 mW, Power Technologies, Inc.) focused to a horizontally elongated elliptical beam spot by cylindrical lenses (horizontal=approximately 80 mm focal length, located approximately 100 mm from the flow cell; vertical=approximately 40 mm focal length, at approximately 40 mm). Each sample particle passing through the laser beam scatters the laser light, and chlorophyll-containing cells emit red (680 nm) fluorescence. One of these signals, usually chlorophyll fluorescence, is chosen to trigger a xenon flash lamp (Hamamatsu L4633) when the signal exceeds a preset threshold. The resulting approximately 1 µs flashes of light are used to provide Kohler illumination of the flow cell. The green component of the light, isolated by an approximately 530 nm bandpass filter, is focused into a randomized fiber optic bundle (approximately 50 µm fibers, approximately 6.35 mm diameter; Stocker-Yale, Inc.). At the fiber optic bundle exit, the light is collected by a lens, passed through a field iris, and focused onto a condenser iris, which is located approximately at the back focal plane of a 10× objective lens (Zeiss CP-Achromat, numerical aperture [N.A.] 0.25), which is in turn focused on the flow cell. A second 10× objective (Zeiss Epiplan, N.A. 0.2) collects the light from both the flash lamp illumination (green) and the laser (red, 635 nm scattered light and 680 nm chlorophyll fluorescence). The green and red wavelengths are separated by a dichroic mirror (630 nm short pass). The green light continues to a monochrome CCD camera (UniqVision UP-1800DS-CL, 1380×1034 pixels). The red light is reflected to a second dichroic mirror (635 LP), which direct the scattered laser light and fluorescence to separate photomultiplier (PMT) modules (Hamamatsu HC 120-05 modified for current-to-voltage conversion with time constant=800 kHz; the PMT for laser scattering also incorporates DC restoration circuitry).

In an embodiment, the optical path is folded, by broadband dielectric mirrors (Thorlabs BB1-E02), on either side of the flow cell to conserve space. The flow cell assembly is fixed to the optical table, while the light source/condenser and objective/PMT/camera assemblies are each mounted on lockable translators (Newport Corp.), providing 3 degrees of freedom for adjustment. The objective focusing translator is remotely controllable. Optical mounting hardware is from Thorlabs, Inc.

In an embodiment, the imaging apparatus is controlled by a PC-104plus computer (Kontron MOPS-LCD7, 700 MHz), running Windows (Microsoft Corporation). Remote operation is carried out via Virtual Networking Computing software (www.realvnc.com) The camera is configured and the syringe pump is programmed by software provided by the manufacturers. All other functions (control, image visualization, and data acquisition) are carried out by custom software, written in Visual Basic 6 (Microsoft Corporation).

Figure 3:
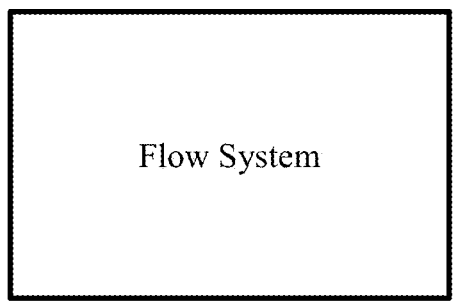
FIG. 3 depicts the modules in one embodiment of the submersible flow imager.
Figure 3:
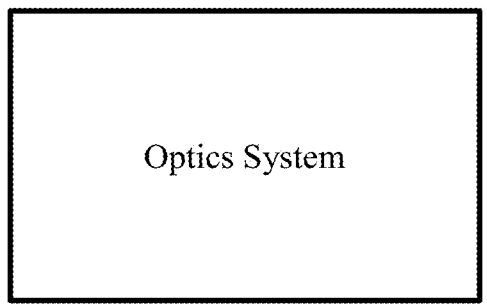
Figure 3:
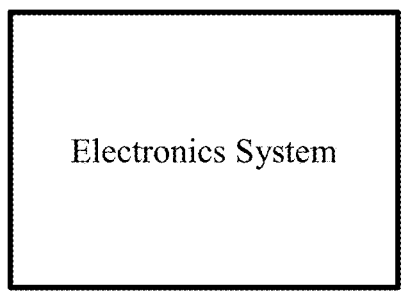

In one embodiment, a custom electronics board amplifies and integrates light scattering and fluorescence signals and also generates control pulses for timing purposes (FIG. 3). The signal from the triggering PMT, which is typically chlorophyll fluorescence, is split, with one part sent to a comparator circuit that produces a trigger pulse if the signal is larger than a preset threshold level. The other part of the signal, and the signal from the other PMT, are delayed by approximately 7 µs (by delay modules from a Coulter Electronics EPICS 750 flow cytometer) and then split and sent to paired linear amplifiers with approximately 25-fold different gains, which increase dynamic range, before integration (Burr-Brown AFC2101). The delay modules allow the pre-trigger portions of the signals to be included in the integration. The end of the integration window is also determined by the comparator, with the provision that the signal remains below the comparator threshold for approximately 20 µs; this allows signals from loosely-connected cells, such as chain diatoms, to be more accurately measured. Comparator output pulses are also integrated to provide an estimate of the duration of each signal. The PMT amplifier inputs are grounded by transistors during flash lamp operation, to avoid baseline distortion by the very large signals from the flashes (FIG. 3A, D).

In another embodiment, the trigger pulse is also sent to a frame grabber board (Matrox Meteor II CL) to begin image acquisition, and, after a delay of approximately 270 µs, to the flash lamp, which illuminates the flow cell for an approximately 1 µs exposure. Integration of light scattering and fluorescence signals is limited to approximately 270 µs to avoid contamination by light from the flash lamp, so integrated signals from particles, cells or chains of cells longer than approximately 600 µm are conservative estimates.

In one embodiment, a multifunction analog-digital (A-D) board (104-AIO16-16E, Acces I/O Products, Inc.) digitizes the integrated laser-derived signals and the duration of the triggering signals, produces analog signals to control the PMT high voltages, and carries out digital I/O tasks (e.g., motor control for focusing the objective and communication between software and hardware, i.e., inhibiting new trigger signals while the current image is being processed).

In an alternative embodiment, to minimize the resources needed for image data storage, the apparatus utilizes a "blob analysis" routine (Matrox Imaging Library) based on edge detection (changes in intensity across the frame) to identify regions of interest in each image. The subsampled images are transferred to a remote computer for storage and further analysis. For taxonomic classification, approach was developed based on a support vector machine framework and several different feature extraction techniques; this approach is described elsewhere (Sosik and Olson 2007), along with the results of automated classification of $1.5 \times 10^6$ images obtained during the apparatus's test deployment in Woods Hole Harbor.

For each particle, 5-9 channels of flow cytometric signal data are stored (integrated and peak signals from 2-4 fluorescence and light scattering detectors, plus signal duration), along with a time stamp (approximately 10-ms resolution). Accumulated images and fluorescence/light scattering data are automatically transferred to the laboratory in Woods Hole approximately every 20 min. The data are analyzed using software written in MATLAB (The Mathworks, Inc.).

In practice, the apparatus can be deployed by divers, who bolt the neutrally buoyant approximately 70-kg instrument to a mounting frame located at approximately 4-m depth on the MVCO Air Sea Interaction Tower (http://www.whoi.edu/science/AOPE/dept/CBLAST/ASIT.html), and connect the power and communications cable, which is equipped with an underwater pluggable connector (Impulse Enterprise, Inc.).

Hydrodynamic focusing causes all the particles in a sample to pass through the submersible flow imager's detection system, allowing the calculation of particle concentration, to a first approximation, by dividing the number of triggers by the volume of water analyzed, as determined by the analysis time and the known rate of flow from the syringe pumps. However, this concentration is an underestimate, because during the time required to acquire and process each image, sample continues to flow through the flow cell, but no new triggers are allowed. The minimum time required by the camera for image acquisition is approximately 34 ms (i.e., approximately 30 frames/sec), but it was determined empirically that with image processing to locate and store the region of interest, at least approximately 86 ms was required by the system; very large particles required even more time. Therefore, the image processing period for each cell was measured using a software timer. By subtracting the sum of these periods from the total elapsed time, the amount of time that was actually spent "looking" for sample particles was determined and used to calculate the sample particle concentration in each syringe sample.

Figure 5:
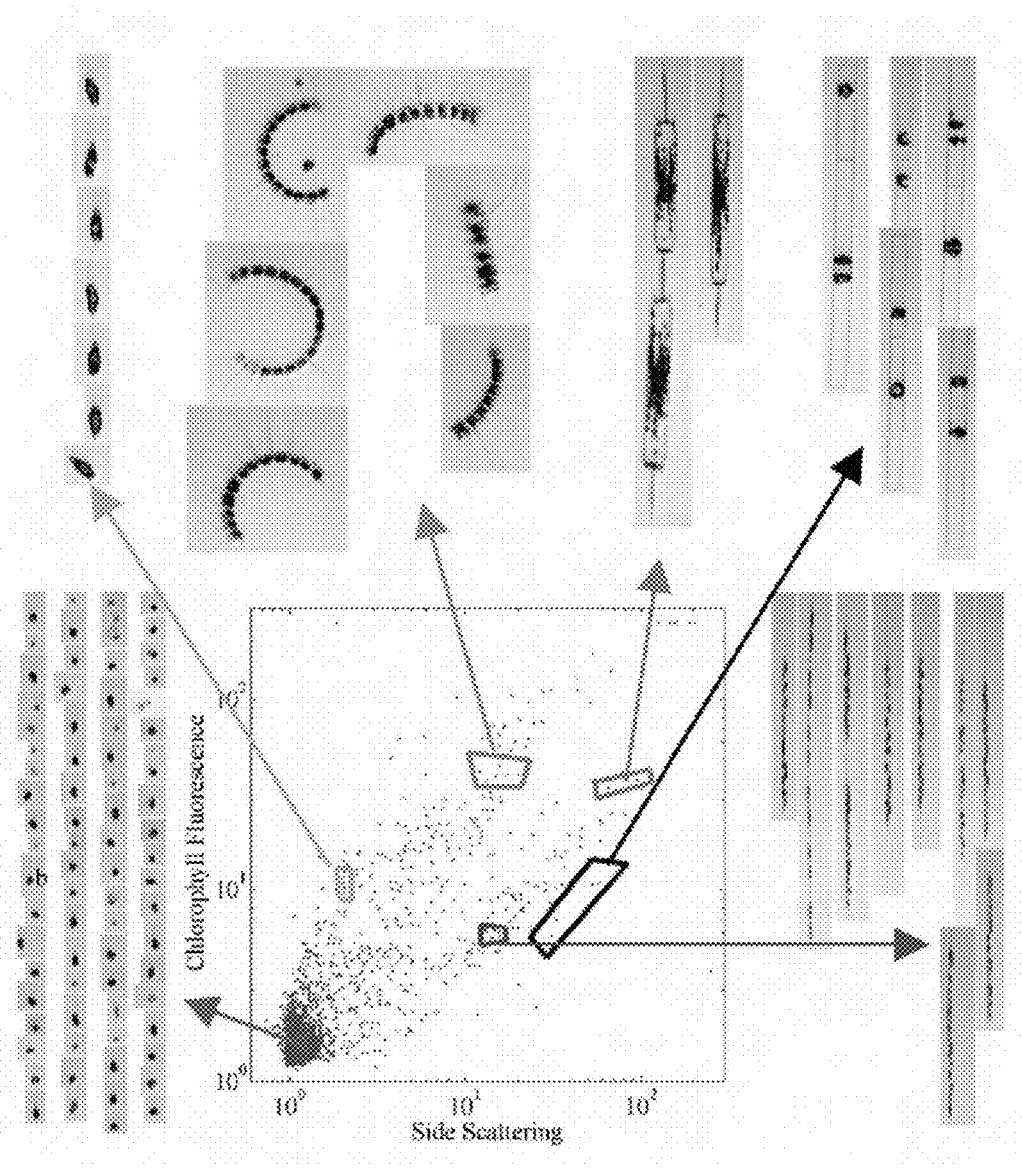
FIG. 5 depicts flow cytometric measurements of side scattering and chlorophyll fluorescence, and selected images of phytoplankton cells in a seawater sample from Woods Hole Harbor, which were analyzed using the imaging apparatus (triggered by chlorophyll fluorescence).

Analysis of seawater samples by the apparatus illustrates some advantages of the approach described herein over conventional flow cytometry and manual microscopic analyses. First, flow cytometric sorting of particles in seawater has shown that light scattering/fluorescence signatures are rarely sufficient to identify nano- or microplankton at the genus or species level. Discrete populations are rarely discernible in a plot of light scattering vs. fluorescence (e.g., see FIG. 5), and even if they are, it is difficult to be sure of their identity without cell sorting and examination. The images associated with the flow cytometric data reinforce this idea—different species do have characteristic light scattering/fluorescence signatures, but these generally form a continuum, and often overlap, and therefore are not very useful in determining species composition. The homogenous populations of cells indicated by the image groupings in FIG. 5 are not random selections, but were obtained by trial-and-error searches of small regions of the plot; other regions show mixtures of species. Thus, imaging allows greater improvement of the accuracy of the identification of different cells.

The ultimate resolution of the optical system is determined by the 10× microscope objective, which has a theoretical resolution of approximately 1 μm. As presently configured, an approximately 20 μm bead spans approximately 68 pixels (approximately 3.4 pixels/μm), so the camera resolution is more than adequate for this objective. However, image quality will be affected by several additional factors in the apparatus, including, particle motion, flash lamp pulse duration, and the location of particles in the flow cell.

Movement of the subject due to sheath flow during the camera exposure will tend to blur the image in the direction of flow. Sample particle velocity was determined (by measuring the image displacement caused by a known change in strobe delay) to be approximately 2.2 m/s, so the subject moves approximately 7.5 pixels during the approximately 1 μs exposure. The effect of this movement is visible in an image of a plastic bead as a thickening of the leading and trailing edges, relative to the upper and lower edges (not shown). In addition, although most of the light energy from the xenon flash is emitted within approximately 1 μs, the flash decays over several μs, which produces a "shadow" downstream of high-contrast subjects. These factors limit the velocity of flow that can be employed, and thus the sampling rate of the instrument. Although a shorter flash, as from an LED or pulsed laser, could be used to address this limitation. Accordingly, in yet another embodiment, the xenon flash is less than approximately 1 μs.

Figure 4:
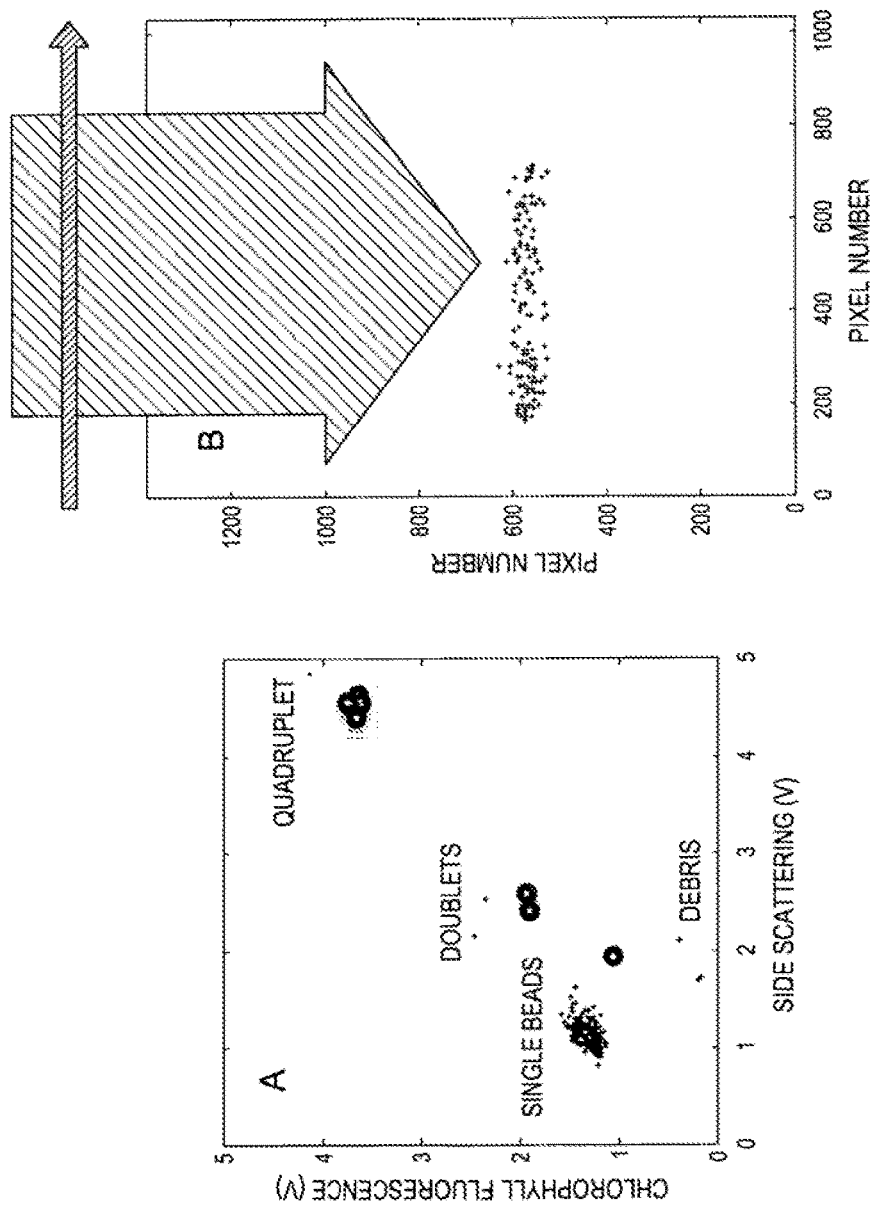
FIG. 4 depicts an analysis of uniform fluorescent beads which illustrates measurements of fluorescence and scattering.

The sample core in the apparatus is approximately 150 μm wide (see FIG. 4B). If it is assumed that the core has the same shape as the channel, the thickness of the core would be approximately 33 μm. This is somewhat greater than the theoretical depth of focus of a 10× objective with N.A. 0.2 to approximately 10 μm. As the thickness of the sample core increases, more particles will be out of focus, which will limit both the sampling rate and the optical resolution that can be employed. Finally, the illumination conditions (e.g., condenser aperture, which is dictated by the amount of light available during the flash) affect the resolution and contrast of the image.

Example 2

Detection of Stained Phytoplankton

In one embodiment, the submersible flow imager provides automated, quantitative measurements of the abundance and properties of nano- and micro-phytoplankton by triggering its imaging system on chlorophyll autofluorescence as individual particles pass through a laser beam. Heterotrophic cells trigger detection if they have recently eaten a phytoplankton or have retained chloroplasts from phytoplankton prey, but heterotrophs lacking chlorophyll fluorescence are not well sampled by this instrument. Scattered laser light can be used as a trigger for all particles, but in practice this strategy is rarely useful because the large numbers of triggers from detrital particles decrease the efficiency of the system for detecting the rarer cells of interest.

In one embodiment, the submersible flow imager solves this issue by applying a stain that causes living cells to become fluorescent and therefore candidates for triggering the system. The submersible flow imager combines several necessary components, which are configured to fit within the submersible housing, and a programmed series of operations:

1) fluorescence emission from the stained sample must be at a different wavelength from that of chlorophyll (which emits in the red, at 680 nm). Fluorescein Diacetate (FDA), which emits fluorescence in the green (530 nm) region of the spectrum was used. FDA is also convenient for use in an in situ instrument because, when dissolved in acetone, it is stable at room temperature. Other stains (e.g., LysoTracker Green®) can also be used.

2) The stain (in one embodiment, FDA) to be used for triggering must be excited with the same laser used for chlorophyll triggering, so the submersible flow imager's 635-nm laser was replaced with a 508 nm diode laser (Power Technology, Inc.). An added benefit of the 508 nm laser is that it excites fluorescence from phycoerythrin, as well as from chlorophyll, enabling discrimination of cells containing phycoerythrin (such as cryptophytes) from other phytoplankton.

3) A new photomultiplier was added to detect the new fluorescence signals. Due to size constraints, the same photomultiplier is used for both stain fluorescence (green) and phycoerythrin fluorescence (orange). In alternating stained/unstained samples, optical filters are changed to isolate signals from green (stain) or orange (phycoerythrin) fluorescence. In a situation where space constraints are lifted (a laboratory instrument), an additional photomultiplier and filter could be added to measure green and orange fluorescence simultaneously.

4) The new signals are analyzed with an unused channel in the submersible flow imager's signal processing module.

5) Changing between optical filters for detecting green (stain) and orange (phycoerythrin) fluorescence is accomplished by a motor-operated cam and lever that slides a 2-place filter holder in the filter slot of the submersible flow imager's detection system module.

6) Staining is accomplished in a custom-built mixing/incubation chamber equipped with a magnetic stirring bar (operated by the submersible flow imager's bead-stirring motor). The chamber is connected to a spare port of the submersible flow imager's distribution valve; an approximately 5-mL water sample is aspirated into the submersible flow imager's syringe and pumped to the chamber for stain addition and incubation, then aspirated again and pumped through the flow cell for analysis and imaging.

7) Stain addition is accomplished by a solenoid-activated micropump (Reet Corp.) which injects a small volume (e.g., approximately 20 microliters) of concentrated stain stock into each water sample before analysis by the submersible flow imager. The small volume is important to allow long term deployments with a practical volume of stain stock (i.e., approximately 6 months at approximately 36 samples/day requires approximately 130 ml stain stock).

8) In one embodiment, to avoid increased background fluorescence due to accumulation of fluorescent stain in the recirculating sheath, two solenoid valves are used to disable sheath recirculation during stained-sample analyses. At these times, external water is introduced to the sheath intake (through a pass-through in an unused plug in submersible flow imager's cap) and the flow cell outlet is directed overboard. During non-staining operations, the sheath fluid is recirculated to conserve filter capacity.

All functions for staining and analysis are under automated control through the submersible flow imager's electronic system and integrated processor and custom control software.

Example 3

Low Relief Embodiments

| Vehicle | Application Requirements | Preferred Configuration or Configuration Requirements |
|---|---|---|
| 3.1 Wave Glider | Accommodate very low vertical clearance in payload bay | Ultra-low relief (≤17 cm) with horizontal Pumping Subsystem |
| 3.2 Autonomous kayak | Accommodate wave-induced tilt/roll, moderate clearance payload bay | Low relief (≤30 cm) with horizontally separated modules, reduced sample core width if needed |
| 3.3 Raft | Moderate clearance payload bay | Low relief (≤30 cm) with horizontally separated modules |

Various embodiments and features of the submersible flow imager have been described in detail with particularity. The utilities thereof can be appreciated by those skilled in the art. It should be emphasized that the above-described embodiments of the submersible flow imager merely describe certain examples implementing the submersible flow imager, including the best mode, in order to set forth a clear understanding of the principles of the invention. Numerous changes, variations, and modifications can be made to the embodiments described herein and the underlying concepts, without departing from the spirit and scope of the principles of the invention. All such variations and modifications are intended to be included within the scope of submersible flow imager, as set forth herein. The scope of the submersible flow imager is to be defined by the claims, rather than limited by the foregoing description of various and alternative embodiments. Accordingly, what is desired to be secured by Letters Patent is the invention as described and differentiated in the claims and all equivalents.

For the purpose of understanding the submersible flow imager, references are made in the text to exemplary embodiments of a submersible flow imager, only some of which are described herein. It should be understood that no limitations on the scope of the invention are intended by describing these exemplary embodiments. One of ordinary skill in the art will readily appreciate that alternate but functionally equivalent components, materials, designs, and equipment may be used. The inclusion of additional elements may be deemed readily apparent and obvious to one of ordinary skill in the art. Specific elements disclosed herein are not to be interpreted as limiting, but rather as a basis for the claims and as a representative basis for teaching one of ordinary skill in the art to employ the present invention.

Reference throughout this specification to features, advantages, or similar language does not imply that all of the features and advantages that may be realized should be or are in any single embodiment. Rather, language referring to the features and advantages is understood to mean that a specific feature, advantage, or characteristic described in connection with an embodiment is included in at least one embodiment. Thus, discussion of the features and advantages, and similar language, throughout this specification may, but do not necessarily, refer to the same embodiment.

Furthermore, the described features, advantages, and characteristics may be combined in any suitable manner in one or more embodiments. One skilled in the relevant art will recognize that the submersible flow imager may be practiced without one or more of the specific features or advantages of a particular embodiment. In other instances, additional features and advantages may be recognized in certain embodiments that may not be present in all embodiments.

Reference throughout this specification to "one embodiment," "an embodiment," or similar language means that a particular feature, structure, or characteristic described in connection with the embodiment is included in at least one embodiment. Thus, appearances of the phrases "in one embodiment," "in an embodiment," and similar language throughout this specification may, but do not necessarily, all refer to the same embodiment.

It should be understood that the drawings are not necessarily to scale; instead, emphasis has been placed upon illustrating the principles of the invention. In addition, in the embodiments depicted herein, like reference numerals in the various drawings refer to identical or near identical structural elements.

Moreover, the terms "substantially" or "approximately" as used herein may be applied to modify any quantitative representation that could permissibly vary without resulting in a change to the basic function to which it is related.

The invention claimed is:

1. A device for imaging particles within liquid suspensions comprising:

a) a flow system, said flow system comprising
   (i) a flow path;
   (ii) a particle suspension means;
   (iii) a substantially horizontal detection path; and
   (iv) a delivery means,
   wherein a liquid suspension comprising particles, travels within said flow path;
b) a detection system, said detection system comprising a core and a flow cell, wherein the detection system detects certain aspects of an imbibed sample introduced into the device;
c) an electronics system, said electronics system comprising a power supply and said electronics system being electronically connected to said flow system and said detection system and said electronics system providing control for both movement of said liquid suspension within said flow path, the detection of said particles, and data storage and transmission; and
d) submersible housing mounted onto an aquatic vehicle that houses at least one of the systems selected from the group comprising the flow system, the detection system, and the electronics system;
   wherein said liquid suspension travels through said flow path and is injected into said substantially horizontal detection path via said delivery means and once in said substantially horizontal detection path, said liquid suspension travels through said core and into said flow cell, where particles can be detected;
   wherein said flow system, said detection system, and said electronics system are located within said submersible housing;
   wherein said device is capable of operation in water; and
e) a bubble minimization means capable of reducing the collection or formation of bubbles in the device;
   wherein said devices is configured in a substantially horizontal orientation without respect to the orientation of the components comprising the systems except for the flow cell which is substantially horizontal while maintaining a flow rate of at least 0.1 ml/min through the flow path; and wherein the systems and their components are each oriented vertically or horizontally such that the overall device is configured to have a vertical relief of less than 36 centimeters;
   wherein the system captures high quality images of plankton, aquatic pollution, and microorganisms in aquatic environments by imbibing liquid samples; and
   wherein the aquatic vehicle is an unmanned vehicle selected from the group comprising ROVs and AUVs.

2. The device of claim 1, wherein the flow system further comprises a non-vertical delivery means.

3. The device of claim 1, wherein the electronics system is substantially spatially removed from the flow system.

4. The device of claim 3, wherein the electronic system is in a separate housing from that of the flow system.

5. The device of claim 1, further comprising a particle staining system.

6. The device of claim 1, further comprising a particle sorting system, said particle sorting system comprising a catcher tube, wherein said catcher tube is positioned below said flow cell, and said catcher tube is located outside of said core while in a resting state but once a particle comprising predetermined parameters is detected in said core by said detection system, said catcher tube enters said core to collect said particle, and said particle is further classified by image processing.

7. The device of claim 1, further comprising a particle concentration system.

8. The device of claim 1, further comprising optical components.

9. The device of claim 8, wherein the optical components are substantially spatially removed from the flow system.

10. The device of claim 1, wherein said housing comprises an attachment means for removably attaching said device either directly or indirectly to the external surface of an aquatic vehicle.

11. The device of claim 10, wherein the flow system is configured so as to collect samples when the device is in towed arrangement.

12. The device of claim 1, wherein said device further comprises at least one module component deployed in the hull of a vessel, vehicle or platform.

13. The device of claim 1, wherein the bubble minimization means comprises a vacuum aspirator that generates a vacuum while the vehicle is in motion to expel dissolved air from the imbibed sample in the device.

14. The device of claim 1, wherein the delivery system further comprises an acoustic focusing element, located before the flow cell in the flow path.

15. A device for imaging particles within liquid suspensions comprising:
   a) a flow system, said flow system comprising
      (i) a flow path;
      (ii) a particle suspension means;
      (iii) a substantially horizontal detection path; and
      (iv) a delivery means,
      wherein a liquid suspension, said liquid suspension comprising particles, travels within said flow path;
   b) a detection system, said detection system comprising a core and a flow cell;
   c) an electronics system, said electronics system comprising a power supply and said electronics system being electronically connected to said flow system and said detection system and said electronics system providing control for both movement of said liquid suspension within said flow path, the detection of said particles, and data storage and transmission; and
   d) a submersible housing capable of mounting onto a vehicle;
   wherein said liquid suspension travels through said flow path and is injected into said substantially horizontal detection path via said delivery means and once in said substantially horizontal detection path, said liquid suspension travels through said core and into said flow cell, where particles can be detected; and
   e) a bubble minimization means capable of reducing the collection or formation of bubbles in the device;
      wherein said flow system, said detection system, and said electronic system are located within said submersible housing;
      wherein said device is capable of operation in water; and
      wherein the components of said device are oriented such that said device comprises a low relief configuration.

16. The device of claim 15, wherein the device height is approximately 36 cm or less.

17. The device of claim 15, wherein said delivery means is in a non-vertical orientation.

18. The device of claim 15, further comprising a particle staining system.

19. The device of claim 15, further comprising a particle sorting system, said particle sorting system comprising a catcher tube, wherein said catcher tube is positioned below said flow cell, and said catcher tube is located outside of said core while in a resting state but once a particle comprising predetermined parameters is detected in said core by said detection system, said catcher tube enters said core to collect said particle.

20. The device of claim 15, wherein said submersible housing comprises an attachment means for removably attaching said device to said vehicle, or a vessel or platform.

21. The device of claim 15, wherein said device is configured such that at least one module is deployed in the hull of a vessel, vehicle, or platform.

22. The device of claim 15, wherein the bubble minimization means capable is selected from the group consisting of the expulsion of fluid comprising the presence of bubbles and a modified vacuum aspirator.

23. The device of claim 15, wherein the device further comprises an acoustic focusing element, located before the flow cell in the flow path.

* * * * *